(12) United States Patent
Hartholt

(10) Patent No.: US 6,761,907 B1
(45) Date of Patent: Jul. 13, 2004

(54) COATED DOSAGE UNITS

(75) Inventor: Gertjan Pieter Hartholt, Uden (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/509,038

(22) PCT Filed: Sep. 21, 1998

(86) PCT No.: PCT/EP98/06042

§ 371 (c)(1),
(2), (4) Date: Mar. 21, 2000

(87) PCT Pub. No.: WO99/15180

PCT Pub. Date: Apr. 1, 1999

(30) Foreign Application Priority Data

Sep. 23, 1997 (EP) ............................................ 97202908

(51) Int. Cl.$^7$ ................................................. A61K 9/28
(52) U.S. Cl. ........................ 424/474; 424/464; 424/465; 424/489; 424/490
(58) Field of Search ................................. 424/490, 479, 424/400, 451, 464, 465, 474, 489

(56) References Cited

U.S. PATENT DOCUMENTS 5,662,936 A * 9/1997 de Haan et al. ............. 424/479

FOREIGN PATENT DOCUMENTS

| EP | 0 273 469 A | | 7/1988 | |
|----|----|----|----|----|
| EP | 0 501 553 A | | 9/1992 | |
| EP | 0 657 161 A | | 6/1995 | |
| EP | 0 659 432 A | | 6/1995 | |
| GB | 1 309 597 A | | 3/1973 | |
| GB | 1309597 | * | 3/1973 | ............ A61K/9/00 |
| GB | 2 195 248 A | | 4/1988 | |

* cited by examiner

Primary Examiner—Thurman K. Page
Assistant Examiner—Robert M. Joynes
(74) Attorney, Agent, or Firm—Allen Turner

(57) ABSTRACT

Dosage units, such as tablet cores and granules, containing a composition comprising a steroid having two hydrogen atoms at position 3 of the steroid skeleton, are coated. While a conventional sugar coating process involves the application of several layers including, as a surface layer, a sugar coat, it was found that a seal coat such as normally used in a sugar coating process can be used as the surface layer for the purpose of preventing the transfer of the steroid out of the composition. From this novel use of a seal coat, novel dosage units result. The process is advantageous, as it requires fewer steps than before.

10 Claims, No Drawings

COATED DOSAGE UNITS

The invention pertains to a dosage unit containing a composition comprising a steroid having two hydrogen atoms at position 3 of the steroid skeleton, such as desogestrel, allylestrenol, ethylestrenol, or lynestrenol, the dosage unit being coated with a surface layer which serves to prevent transfer of the steroid out of the composition.

Such dosage units are known from EP 0 659 432, wherein a sugar coat is applied as the surface layer. A sugar coat in itself is a known coating for masking unpleasant tastes and odours, to protect an ingredient from decomposition as a result of exposure to air, light, or moisture, or to improve tablet appearance and to increase aesthetic appeal. As described, the sugar coat was found to solve another problem, viz, that of the tendency of apolar active compounds, such as the above steroids, to transfer out of tablets and granules comprising them.

The coated dosage units of EP 0 659 432 are disclosed to be prepared by a process comprising, after the conventional making of tablet cores and granules, the steps of optional sealing, followed by subcoating, syruping, finishing and optionally polishing. The sealing step refers to the application of a seal coat directly over the tablet cores and granules. This step is a regular part of sugar-coating processes such as described in *Remington's* (18th edition, A. R. Gennaro ed., Mack Publishing Co. Easton, Pa. 1990), pages 1667–1668. In such processes the seal coat primarily serves the purpose of separating the tablet ingredients and water, which is a major constituent of the coating formulation used thereafter. A secondary function is to strengthen the tablet core.

It has now been found that coated dosage units of the above type can be made in a more economical way, while still preventing the transfer of the steroid out of the composition.

For, surprisingly, the aforementioned seal coat when used as an end-layer, i.e., as a surface layer coating the dosage unit, suitably serves this purpose.

Hence, the invention is a dosage unit of the above type, with the surface layer being a sealing coat as normally used in a sugar coating process, hereinafter referred to as "seal coat", in brief. Thus, the invention resides in a novel pharmaceutical end-product which has, as its outer surface, a layer that has only been known as an intermediate layer rather than as an end-layer.

It was found that a seal coat almost completely prevents the steroid of the above type from being transferred out of the dosage unit.

In another respect, the invention resides in more economical process of preparing a coated dosage unit comprising making a dosage unit containing a composition comprising a steroid having two hydrogen atoms at position 3 of the steroid skeleton and subjecting the dosage unit to coating steps comprising the application of a seal coat. For, such a process being known, the invention is that any further coating steps after the application of the seal coat are refrained from. Thus, the invention resides in a process of a known type, wherein, surprisingly, a step considered in the art to be crucial, can be refrained from.

In yet another respect, the invention resides in the unexpected new use of a seal coat known in itself Thus, the seal coat, applied on a dosage unit containing a composition comprising a steroid having two hydrogen atoms at position 3 of the steroid skeleton, is used for the purpose of preventing transfer of the steroid out of the composition.

The tendency of the apolar active compound to transfer out of the composition is of particular concern when the tablet cores or granules comprise very low dosages of said apolar active compounds. This is the case in tablets and granules comprising the progestagen desogestrel, allylestrenol, ethylestrenol, or lynestrenol. Tablets having desogestrel as active ingredient comprise usually 25–150 aeg, and typically 25, 50, 75, 100, or 150 aeg of desogestrel. Tablets having allylestrenol as active ingredient comprise usually 10–75 mg, and typically 25 mg of allylestrenol, and tablets having ethylestrenol or lynestrenol as active ingredient comprise usually 0.5–10 mg, and typically 2.0 or 2.5 mg of ethylestrenol or lynestrenol. For desogestrel, allylestrenol, ethylestrenol, or lynestrenol, which are used as active ingredient in contraceptive or HRT (hormone replacement therapy) drugs, this is not acceptable in view of their safety and reliability. A loss of for example 10% of the active substance within the shelf-life has therefore a dramatic effect on the amount of active ingredient in the tablet, and could lead to a tablet having less than the treshold amount of active ingredient to exert full activity. It is now found that sugar-coating can be used for other purposes than preventing moisture to enter the tablet or granule; it also can be used to prevent the transfer of a steroid having two hydrogen atoms at position 3 of the steroid skeleton, such as desogestrel, allylestrenol, ethylestrenol, or lynestrenol from the tablet or granule to the environment. The sugar-coated dosage unit apart from the steroid having two hydrogen atoms at position 3 of the steroid skeleton, such as desogestrel, allylestrenol, ethylestrenol, or lynestrenol can further comprise an estrogen.

Examples of estrogens include ethinyl estradiol, β-estradiol, mestranol (17-à-ethinyl estradiol 3-methylether), estrone, estradiol, estradiol valerate and other estradiol esters, and other compounds with estrogenic activity. Ethinyl estradiol and β-estradiol are the preferred estrogen.

As used herein, "transfer" includes any process in which the steroid having two hydrogen atoms at position 3 of the steroid skeleton prematurely leaves the dosage unit.

The term "dosage unit" generally refers to physically discrete units suitable as unitary dosages for humans or animals, each containing a predetermined quantity of active material (e.g. estrogen and/or desogestrel) calculated to produce the desired effect. Examples of such dosage units are tablets, granulates, powders, and pills.

Methods and compositions for making various dosage units excipients and granules are known to those skilled in the art. For example, methods and compositions for making tablets and pills are described in Remington's (18th edition, A. R. Gennaro Ed., Mack Publishing Co. Easton, Pa., 1990), at pages 1633 through 1665.

The concentration of steroid or steroids included in the tableting mixture, and eventually the dosage unit, will of course depend on the particular steroid's potency, its intended use, and the eventual mass of the dosage unit. The amount of a steroid or steroids used in a dosage unit will be well-known to those skilled in the art.

A tablet core or granule according to the invention comprise typically a diluent and optionally a binder. Preferably the tablet core or granulate will also include a disintegrating agent.

Diluents or "filler excipients" are agents added to dosage units to increase the granules' and resulting dosage units' bulk. The preferred diluent for use in this regard is lactose. Other diluents include mannitol, sorbitol, cellulose, xylitol, dextrose, fructose, calcium phosphate, NaCaPO4, sucrose, and mixtures thereof. The diluent will typically make up from 70 to 95% by weight of the resulting steroid loaded granules.

Binders are agents used to impart cohesive properties to the granules, resulting in more physically stable dosage units, and include hydroxypropylcellulose, amylopectin, starch, povidone (polyvinylpyrrolidone), hydroxypropylmethylcellulose, gelatin, and starch based binders. The preferred binder for use with the invention is amylopectin. The binder will typically make up from 0.5 to 5% by weight of the resulting steroid loaded tablet cores or granules.

Disintegrating agent or "disintegrators" are substances or mixtures of substances added to a tablet to facilitate its breakup or disintegration after administration. Typically such agents are modified or unmodified starches, clays, cross-linked PVP, modified or un-modified celluloses, gums or algins. The presently most preferred agents are corn starch, potato starch, and wheat starch. Disintegrators will typically make up from 5 to 50%, preferably 5 to 15%, by weight of the resulting tableting mixture.

The tableting mixture may be prepared in a mixer. However, the tableting mixture can also be made in a fluidized bed granulator, and then later added to the mixer for later loading with steroid.

Mixers for use with the invention are readily commercially available and are capable of mixing or blending the dry ingredients with a solvent containing the steroid or steroids. Vacuum mixers which are closed to the outside environment are preferred for workers' safety and environmental reasons since the solvent is not released into the atmosphere, and can be collected for re-use.

The "wet" portion added to the carrier will preferably consist of the steroid or steroids, an anti-oxidant, and a lubricant all dissolved or suspended in a solvent.

Lubricants are agents which improve the rate of flow of the tablet granulation, prevent adhesion of the tablet material to the surface of dies and punches, reduce interparticle friction, and facilitate the ejection of the tablets from the die cavity. Commonly used lubricants are talc, long chain fatty acids, magnesium stearate, stearic acid, calcium stearate, polyethylene glycol, palmitic acid, and hydrogenated vegetable oils. The lubricant will typically make up from 0.25 to 3% by weight of the resulting granules.

Solvents for use with the invention are preferably those having a sufficiently low boiling point at the pressures attainable in the vacuum mixer to evaporate off during the process. These include acetone, dichloromethane, ethanol, methanol, isopropanol, and mixtures thereof. When miscible these organic solvents may be mixed with water. The binder need not be very soluble in the solvent.

A sufficient amount of solvent will be used to dissolve the steroid or steroids, and when present the lubricant and anti-oxidant, and to wet the carrier without impairing the flow properties. Thus the amount of solvent used in the process will depend upon the potency and solubility characteristics of the particular steroid or steroids in the particular solvent, the solubility of the other components in the solvent, and the size of the batch of carrier to be wetted. Solvents will typically make up from 5 to 20% by weight of the mixture of solution and carrier.

After removal of the solvent, a flow enhancer is preferably mixed with the drug loaded tableting mixture. The flow enhancer (e.g. talc or colloidal silicon dioxide) acts to prevent the tableting mixture from clumping. Flow enhancers will typically make up from 0.1 to 3% by weight of the resulting mixture.

The use of other conventional additives or "further excipients", e.g. colorants, stabilizers or anti-oxidants, is contemplated. Stabilizers such as EDTA, polyethylene glycol (PEG), and butylated hydroxytoluene (BHT), may also be included if desired, although it is not required. The presently most preferred anti-oxidant for use with the invention is dl-à-tocopherol. Other medicinal agents (e.g. à-estradiol) may also be included in the formulation.

The tableting mixture may also be obtained by a solvent-free process. The active ingredients may be dry-mixed, for instance with spray-dried lactose, to obtain a tableting mixture free of trace amounts of solvent. Suitable processes for dry-mixing desogestrel are described inter alia in U.S. Pat. No. 3,432,507 and EP-A-503,521, which are included by reference.

The tableting mixture may then be tabletted by means well-known to those skilled in the art.

For the coating layer according to the present invention those substances and compositions can be used which are normally applied as a sealing coat. Sealing coats used in sugar coating processes usually consist of alcoholic solutions (approximately 10–30% solids) of resins such as shellac, zein, cellulose acetate phthalate, or polyvinyl acetate phthalate. Shellac is preferably used in the form of a shellac-based formulation containing polyvinylpyrrolidone. Other suitable polymeric solutions can be used as a seal coat, such as a copolymer of dimethylaminoethyl methacrylate and methacrylic acid ester (Eudragit®). The seal coat preferably is Eudragit® E12.5 or Sepifilm® SN. The latter is a composition comprising int.al. shellac.

According to the invention, use is made of such a seal coat, applied on a dosage unit containing a composition comprising a steroid as described hereinbefore, for the purpose of preventing transfer of the steroid out of the composition. Although the best results were obtained when using Eudragit®, which therefore is the most preferred seal coat used as a coating layer, the invention in principle resides in the finding that seal coats in general can be used for said purpose.

The coating layer can be applied using the same apparatus as in a sugar coating process. As described in EP 659 432, this should be a facility in which temperature, moisture, and dust can be closely controlled. Large coating pans, preferably of stainless steel and usually about 1 m in diameter and 75 cm in depth, are used. Many other variations and sizes are also workable. In particular, the Accela-Cota and Pellegrini pans known in the art represent a suitable pan design.

Hence, the process of the present invention can be carried out as a sugar-coating process which is terminated at an early stage, viz. after the application of a seal coat. At least two seal coats are usually necessary, but as many of six or more seal coats can be applied. Dusting compounds as asbestos-free talc and terra alba can be added to prevent the tablet cores and granules from adhering to one another and to the pan during the seal coat.

The invention is illustrated further with reference to the following examples.

EXAMPLE 1

Coated tablets were produced with amylopectin cores of 80 mg having a diameter of 6 mm and a radius of curvature of 9 mm. The composition of the cores is given in the Table. The coating layer was Eudragit® E12.5:12.5% dimethylaminoethyl methacrylate and methacrylic acid ester copolymer, 87.5% 2-propanol.

The amylopectin active granulate was produced on a 50 kg scale using the method described in EP 659 432. A 3% overage of the actives was used to correct for the losses on 50 kg scale. The granulate was compressed into tablets having the above dimensions.

TABLE

Composition of the cores

| Ingredients | mg/core. |
|---|---|
| desogestrel | 0.150 |
| ethinylestradiol | 0.030 |
| di-α-tocopherol | 0.080 |
| magnesium stearate | 0.40 |
| potato starch | 8.08 |
| amylopectin | 1.43 |
| lactose to: | 80.00 |

A quantity of 3 kg of the tablet cores was loaded in a sugar coating pan. To the rotating tablet bed were added, in quantities of approximately 90 g, 360 g of a solution of 45 g of the copolymer of dimethylaminoethyl methacrylate and methacrylic acid ester in 2-propanol. Talc was dry added to prevent sticking of the tablet cores. Subsequently the tablet cores were unloaded and dried at 30° C. overnight. The composition of the coating layer was calculated to be 1,20 mg of dimethylaminoethyl methacrylate and methacrylic acid ester copolymer and 4,80 mg of talc.

The amount of desogestrel transfer out of the tablets was determined with a sublimation test. In this test the tablets were stored for 72 hours at a pressure of 150 mbar, at a temperature of 70° C., and the transfer of desogestrel from the tablet was measured.

The measured percentage of desogestrel transferred from the tablets was 0.3%.

EXAMPLE 2

Coated tablets were produced with the same amylopectin cores as in Example 1 and having the same composition. The coating layer was Sepifilm®*(E) SN: shellac 20–26%, monoglycerides acetylated 7–11%, polyvinyl pyrrolidone K30 <5%, ethyl alcohol 60–70%.

A quantity of 3 kg of the tablet cores was loaded in a sugar-coating pan. To the rotating tablet bed were added, in quantities of approximately 90 g, 260 g Sepifilm SN. Talc was dry added to prevent sticking of the tablet cores. Subsequently the tablet cores were unloaded and dried at 30° C. overnight. The composition of the coating layer was calculated to be 2,40 mg of shellac, monoglycerides acetylated and polyvinyl pyrrolidone K30, and 4,80 mg of talc.

The amount of desogestrel transfer out of the tablets was determined as above.

The measured percentage of desogestrel transferred from the tablets was 0.7%.

EXAMPLE 3 (Comparative)

Tablets were produced having the same composition and dimensions as in the preceding examples. The coating process was omitted, so as to produce uncoated tablets.

The amount of desogestrel transfer out of the tablets was determined as above.

The measured percentage of desogestrel transferred from the tablets was 13.9%.

What is claimed is:

1. A dosage unit suitable for administration to a subject said dosage unit consisting of:

a pharmaceutical composition that comprises a steroid having two hydrogen atoms at position 3 of a steroid skeleton, and as an end-layer, a seal coat that prevents transfer of the steroid out of the pharmaceutical composition, wherein the seal coat is normally used in a sugar coating process and comprises a resin that is not HPMC, or comprises a copolymer of dimethylaminoethyl methacrylate ad methacrylic acid ester, the seal coat being applied directly onto the surface of the dosage unit.

2. The dosage unit according to claim 1, wherein the seal coat is shellac.

3. The dosage unit according to claim 1, wherein the steroid is desogestrel, allyestrenol, ethylestrenol, or lynestrenol.

4. The dosage unit according to claim 1, wherein the pharmaceutical composition further comprises an estrogen.

5. The dosage unit according to claim 1, wherein the dosage unit is a tablet core or granule.

6. A process of coating the dosage unit according to claim 1, said process consisting of the steps of:

providing a dosage unit containing a composition comprising a steroid having two hydrogen atoms at position 3 of a steroid skeleton, and applying a seal coat to the dosage unit to form a coated dosage unit, wherein the application of the seal coat is the final step.

7. A method for preventing transfer of a steroid having two hydrogen atoms at position 3 of a steroid skeleton from a pharmaceutical dosage unit suitable for administration to a subject, said method consisting of the step of:

applying to said pharmaceutical dosage unit a seal coat normally used in a sugar coating process, which seal coat is a resin other than HPMC or is a copolymer of dimethylaminoethyl methacrylate and methacrylic acid ester.

8. A dosage unit suitable for administration to a subject, said dosage unit consisting of:

a pharmaceutical composition that comprises a steroid having two hydrogen atoms at position 3 of a steroid skeleton, and, as end layers, at least two seal coats that prevent transfer of the steroid out of the pharmaceutical composition, wherein the seal coats are normally used in a sugar coating process and comprise a resin that is not HPMC, or comprise a copolymer of dimethylaminoethyl methacrylate and methacrylic acid ester, the seal coats being applied directly onto the surface of the dosage unit.

9. A process of coating the dosage unit according to claim 1, said process consisting of the steps of:

providing a dosage unit containing a composition comprising a steroid having two hydrogen atoms at position 3 of a steroid skeleton, and, applying at least two seal coats to the dosage unit to form a coated dosage unit, wherein the application of the seal coats is the final step.

10. A method of preventing transfer of a steroid having two hydrogen atoms at position 3 of a steroid skeleton from a pharmaceutical dosage unit suitable for administration to a subject, said method consisting of the step of:

applying to said pharmaceutical dosage unit at least two seal coats normally used in a sugar coating process, which seal coats are a resin other than HPMC or are a copolymer of dimethylaminoethyl methacrylate and methacrylic acid ester.

* * * * *